United States Patent [19]

Kleiner

[11] Patent Number: 5,679,842
[45] Date of Patent: Oct. 21, 1997

[54] PROCESS FOR THE PREPARATION OF AMINOMETHANEPHOSPHONIC ACID AND AMINOMETHYLPHOSPHINIC ACIDS

[75] Inventor: Hans-Jerg Kleiner, Kronberg/Taunus, Germany

[73] Assignee: Hoechst Aktiengesellschaft, Frankfurt, Germany

[21] Appl. No.: 344,528

[22] Filed: Nov. 23, 1994

Related U.S. Application Data

[63] Continuation of Ser. No. 969,165, filed as PCT/EP91/01494, Aug. 7, 1991, abandoned.

[30] Foreign Application Priority Data

Aug. 17, 1990 [DE] Germany ............... 40 26 027.5

[51] Int. Cl.$^6$ .................. C07F 9/02; C07F 9/28
[52] U.S. Cl. .................................. 562/15
[58] Field of Search .............................. 562/15

[56] References Cited

U.S. PATENT DOCUMENTS

| | | | |
|---|---|---|---|
| 2,328,358 | 8/1943 | Pitman | 562/15 |
| 4,368,162 | 1/1983 | Maier | 562/15 |

FOREIGN PATENT DOCUMENTS 0370992  5/1990  European Pat. Off. .

OTHER PUBLICATIONS

Chemical Abstracts, vol. 107, p. 714, 39933j: "A convenient synthesis of aminomethylphosphonic acid", 1987.
Soroka, Synthesis 1989, pp. 547–548.
March Adv. Org. Chem. 3rd Ed (1985) pp. 338–339.

*Primary Examiner*—Joseph Conrad
*Attorney, Agent, or Firm*—Curtis, Morris & Safford, P.C.

[57] ABSTRACT

Aminomethanephosphonic acid and aminomethylphosphinic acids are interesting as biologically active compounds or as intermediates for the preparation of biologically active compounds. According to the invention, such compounds of the formula I

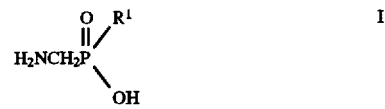

in which $R^1$ is OH, $C_1$–$C_4$-alkyl or phenyl, can be prepared in a technically simple manner by reacting compounds of the formula II

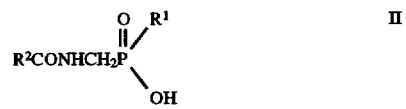

in which $R^2$ is H, $C_1$–$C_6$-alkyl, benzyl, phenyl, optionally substituted by $C_1$–$C_4$-alkyl, -alkoxy and/or halogen, and $R^1$ is as defined above, with water, at 80° to 300° C.

25 Claims, No Drawings

PROCESS FOR THE PREPARATION OF AMINOMETHANEPHOSPHONIC ACID AND AMINOMETHYLPHOSPHINIC ACIDS

This application is a continuation of application Ser. No. 07/969,165, filed as PCT/EP91/01494 Aug. 7, 1991, now abandoned.

Herbicidal and plant-growth-regulating actions are known of aminomethanephosphonic acid; aminomethylphosphinic acids are also industrially valuable compounds having a biological activity or can be used as intermediates for the preparation of biologically active compounds (see the article by L. Maier "Advances in the Chemistry of Aminophosphinic Acids" in the periodical "Phosphorus and Sulfur" 1983, Vol. 14, p. 295–322, in particular 317–323 and literature cited therein). Aminomethanephosphonic acid is furthermore valuable as an intermediate for the preparation of N-phosphonomethylglycine (see EP-A-214,578).

Aminomethanephosphonic acid can be prepared from acyl-aminomethanephosphonic acids by hydrolysis with hydrochloric acid (U.S. Pat. No. 2,304,156; U.S. Pat. No. 2,328,358; M. Soroka, Synthesis 1989, 547). It is a disadvantage of this process that the aminomethanephosphonic acid can only be obtained in high yields during working-up when special measures are applied. For example, M. Soroka describes working-up with the aid of pyridine or propylene oxide, which cause the separation of hydrogen chloride from the aminomethanephosphonic acid. Another disadvantage is that, without complicated ultrapurification, the acylaminomethanephosphonic acids contain traces of formaldehyde, due to the production process. The treatment with hydrochloric acid in the hydrolysis then results in the formation of bischloromethyl ether as undesirable by-product, which has been identified clearly as a carcinogenic working substance. There is therefore a demand for hydrolysis processes which can be carried out on an industrial scale and which exclude the formation of the by-product bischloromethyl ether.

The invention relates to a process for the preparation of compounds of the formula I

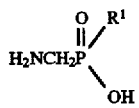

in which $R^1$ is hydroxyl, $C_1$–$C_4$-alkyl, preferably $C_1$–$C_2$-alkyl, in particular methyl, or is phenyl, which comprises reacting acylaminomethanephosphonic or acylaminomethylphosphinic acids of the formula II

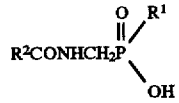

in which $R^2$ is hydrogen, alkyl having 1 to 6 carbon atoms, preferably 1 to 3 carbon atoms, or is benzyl or phenyl, unsubstituted or substituted by one or more radicals from the group comprising $C_1$–$C_4$-alkyl, $C_1$–$C_4$-alkoxy and halogen, and $R^1$ is as defined above, with water, at 80° to 300° C., preferably 150° to 250° C.

Some of the starting substances of the formula II are known, or some are accessible analogously to known methods. For example, the acylaminomethanephosphonic acids of the formula II can be prepared from N-(hydroxymethyl) amides and $PCl_3$ (see U.S. Pat. No. 2,328,358; U.S. Pat. No. 2,304,156 or M. Soroka, Synthesis 1989, 547 and literature cited therein).

The acylaminomethanephosphonic acids as well as the acylaminomethylphosphinic acids of the formula II can also be prepared by the process in German Patent Application P 4,026,026.7.

Examples of preferred starting substances of the formula II are formylaminomethanephosphonic acid, acetylaminomethanephosphonic acid, benzoylaminomethanephosphonic acid, (acetylaminomethyl)(methyl)phosphinic acid and (benzoylaminomethyl)(phenyl)phosphinic acid.

The starting substances of the formula II are treated with water, if appropriate with an excess of water, and the mixture is brought to reaction temperature, and it may be necessary to carry out this process under pressure, as a function of the temperature.

The extent of the excess of water is not particularly critical for the reaction; for example, for reasons of better handling, it may be advantageous to use a 2 to 30 molar, preferably 10 to 25 molar, excess of water. The reaction temperatures are 80° to 300° C., preferably 150° to 250° C. The reaction times depend on the substrate, reaction temperature and pressure and are generally in the range from 5 to 40 hours, preferably 10 to 35 hours.

When the reaction is complete, working-up can be carried out in a simple manner, for example by removing the carboxylic acid as a solid (for example benzoic acid) or by distillation (for example acetic acid). The resulting aminomethanephosphonic acid, or aminomethylphosphinic acids, generally already have high purity. If appropriate, they can be obtained in ultrapure form by customary methods, preferably by crystallization.

EXAMPLE 1

20 g (0.093 mol) of benzoylaminomethanephosphonic acid and 20 g of water were placed in a sealed tube and maintained at 200° C. for 20 hours. After cooling, the reaction material was digested with 100 ml of water. The benzoic acid was subsequently filtered off with suction. The filtrate was concentrated in vacuo by distillation until it had reached an internal temperature of 75° C. There remained 10.3 g (100% of theory) of aminomethanephosphonic acid which, according to $^{31}$P-NMR spectrum analysis, had a purity of 95%.

EXAMPLE 2

20 g (0.093 mol) of benzoylaminomethanephosphonic acid and 20 g of water were placed in a sealed tube and maintained at 150° C. for 20 hours. After cooling, the reaction material was then digested with methanol and filtered off with suction. 8.2 g (80% of theory) of aminomethanephosphonic acid of a decomposition point of 310° C. were obtained.

EXAMPLE 3

20 g (0.093 mol) of benzoylaminomethanephosphonic acid and 20 g of water were refluxed for 30 hours. After cooling, the reaction material was digested with 100 ml of methanol and filtered off with suction. 5.3 g (52% of theory) of aminomethylphosphonic acid of a decomposition point of 275° C. were obtained. Unreacted benzoylaminomethanephosphonic acid could be isolated from the filtrate.

EXAMPLE 4

21.3 g (0.1 mol) of benzoylaminomethylmethylphosphinic acid and 42 g of water were placed in a sealed tube and maintained at 200° C. for 20 hours. After cooling, the mixture was digested with water, and benzoic acid was removed by filtration with suction. The filtrate was evaporated to dryness in vacuo. The crystalline residue was digested with methanol and filtered off with suction. 8 g (73% of theory) of aminomethylmethylphosphinic acid of a melting point of 255°–261° C. were obtained.

EXAMPLE 5

20 g (0.073 mol) of benzoylaminomethylphenylphosphinic acid and 40 ml of water were placed in a sealed tube and maintained at 225° C. for 23 hours. The benzoic acid was then removed by filtration with suction, followed by rinsing with water. The filtrate was concentrated to dryness in vacuo. There remained 12.5 g (100% of theory) of crude aminomethylphenylphosphinic acid. After digestion with methanol, the substance obtained had a melting point of 276°–278° C.

EXAMPLE 6

14.4 g (0.094 mol) of acetylaminomethanephosphonic acid and 28 g of water were fed into a sealed tube and maintained at 200° C. for 20 hours. The mixture was then cooled, and the resulting reaction solution was freed in vacuo from water and acetic acid. The residue was digested with a mixture of 30 ml of methanol and 1 ml of water. 9.6 g (92% of theory) of aminomethanephosphonic acid of a decomposition point of 270°–278° C. were obtained.

I claim:

1. A process for the preparation of compounds of the formula I

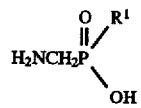
I in which $R^1$ is hydroxyl, $C_1$–$C_4$-alkyl or phenyl, which consisting essentially of contacting acylaminomethanephosphonic or acylaminomethylphosphinic acids of the formula II

II in which $R^2$ is hydrogen, alkyl having 1 to 6 carbon atoms, benzyl or phenyl, unsubstituted or substituted by one or more radicals selected from the group consisting of $C_1$–$C_4$-alkyl, $C_1$–$C_4$-alkoxy and halogen, and $R^1$ is as defined above, with water, at 80° to 300° C. without adding acid.

2. The process as claimed in claim 1, in which $R^1$ is hydroxyl.

3. The process as claimed in claim 2, wherein the reaction temperature is 150° to 250° C.

4. The process as claimed in claim 2, wherein $R^2$ is $C_1$–$C_3$-alkyl, benzyl or phenyl.

5. The process as claimed in claim 4, wherein the reaction temperature is 150° to 250° C.

6. The process as claimed in claim 5, wherein there is about a 2 to 30 molar excess of water, based on 1 mole of compound of formula II.

7. The process as claimed in claim 1, in which $R^1$ is methyl, ethyl or phenyl.

8. The process as claimed in claim 7, wherein the reaction temperature is 150° to 250° C.

9. The process as claimed in claim 7, wherein $R^2$ is $C_1$–$C_3$-alkyl, benzyl or phenyl.

10. The process as claimed in claim 9, wherein the reaction temperature is 150° to 250° C.

11. The process as claimed in claim 10, wherein there is about a 2 to 30 molar excess of water, based on 1 mole of compound formula II.

12. The process as claimed in claim 1, in which $R^2$ is H, $C_1$–$C_3$-alkyl, benzyl or phenyl.

13. The process as claimed in claim 1, in which $R^2$ is phenyl.

14. The process as claimed in claim 1, in which the reaction temperature is 150° to 250° C.

15. The process as claimed in claim 1, in which a 2 to 30 molar excess of water, based on 1 mol of compound of the formula II, is employed.

16. The process as claimed in claim 1, in which the reaction time is in the range from 5 to 40 hours.

17. The process as claimed in claim 1, wherein the compound of formula (II) and water are reacted, substantially in the absence of any other component in the reaction mixture.

18. The process as claimed in claim 17, wherein the reaction is carried out in a sealed tube.

19. The process as claimed in claim 17, wherein the reaction temperature is 150° to 250° C.

20. The process as claimed in claim 17, wherein 2 to 30 molar excess of water, based on 1 mole of compound of formula (II), is employed.

21. A process for the preparation of a compound of formula I

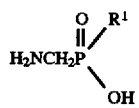

in which $R^1$ is hydroxyl, $C_1$–$C_4$-alkyl, or phenyl, which process consists of contacting acylaminomethanephosphonic or acylaminomethylphosphinic acid of formula II

in which $R^2$ is hydrogen, alkyl having 1 to 6 carbon atoms, benzyl or phenyl, unsubstituted or substituted by one or more radicals selected from the group consisting of $C_1$–$C_4$-alkyl, $C_1$–$C_4$-alkoxy and halogen, and $R^1$ is as defined above, with water, at a temperature of 80° to 300° C.

22. The process of claim 21 wherein the temperature is 150° to 250° C.

23. The process of claim 22 wherein the contacting is for 5 to 40 hours.

24. The process of claim 23 wherein the contacting is at 150° C. for 20 hours.

25. A process for the preparation of a compound of formula I

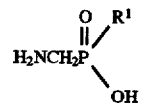

in which $R^1$ is hydroxyl, $C_1$–$C_4$-alkyl, or phenyl, which process consists essentially of contacting, for 5 to 40 hours, acylaminomethanephosphonic or acylaminomethylphosphinic acid of formula II

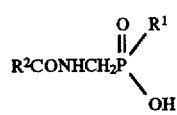
in which $R^2$ is hydrogen, alkyl having 1 to 6 carbon atoms, benzyl or phenyl, unsubstituted or substituted by one or more radicals selected from the group consisting of $C_1$–$C_4$-alkyl, $C_1$–$C_4$-alkoxy and halogen, and $R^1$ is as defined above, with water, at a temperature of above 150° to up to 250° C., without adding acid.
* * * * *